US00PP33312P2

(12) United States Plant Patent
Van Swieten

(10) Patent No.: US PP33,312 P2
(45) Date of Patent: Aug. 3, 2021

(54) ***PHALAENOPSIS* ORCHID PLANT NAMED 'PHALIPUE'**

(50) Latin Name: ***Phalaenopsis* hybrid**
Varietal Denomination: PHALIPUE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/016,956

(22) Filed: Sep. 10, 2020

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALIPUE', particularly characterized by reddish-purple flowers with white centers and greenish yellow-white lips, flat flower shape in lateral view, calluses with no pattern, and is propagated by meristem tissue culture, is disclosed.

3 Drawing Sheets

Genus and species: *Phalaenopsis* hybrid.
Variety denomination: 'PHALIPUE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALIPUE'.

The new *Phalaenopsis* plant is a product of a planned breeding program conducted by the inventor in Bleiswijk, the Netherlands. The objective of this breeding program was to create a new *Phalaenopsis* plant with attractive, reddish-purple flowers with white centers and greenish yellow-white lips, suitable for potted plant production.

The new *Phalaenopsis* plant 'PHALIPUE' is a result of cross-pollination made by the inventor in November 2012 in Bleiswijk, the Netherlands, of the proprietary female, or seed parent, *Phalaenopsis* hybrid '01-2994' (unpatented) with the proprietary male, or pollen parent, *Phalaenopsis* hybrid '32526-01' (unpatented).

The new *Phalaenopsis* was selected by the inventor as a single plant within the progeny of the stated cross-pollination in a controlled greenhouse in Bleiswijk, the Netherlands, in July 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 20, 2019 (Application no. 2019/2313), by Applicant who obtained the subject matter disclosed directly from the inventor. 'PHALIPUE' has not been made publicly available or sold anywhere in the world prior to the effective filing date of this application with the exception of sales or disclosures made one year or less before the effective filing date of this claimed invention by Applicant who obtained 'PHALIPUE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALIPUE' as a new and distinct variety of *Phalaenopsis* plant:

1) Reddish-purple flowers with white centers and greenish yellow-white lips;
2) Flower shape in lateral view is flat; and
3) Callus has no pattern; is even.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in August 2020. Colors in the photographs may differ from the color values cited in the detailed botanical description, which accurately describe the actual colors of the new variety.

DESCRIPTION OF THE NEW VARIETY

Figure 1:
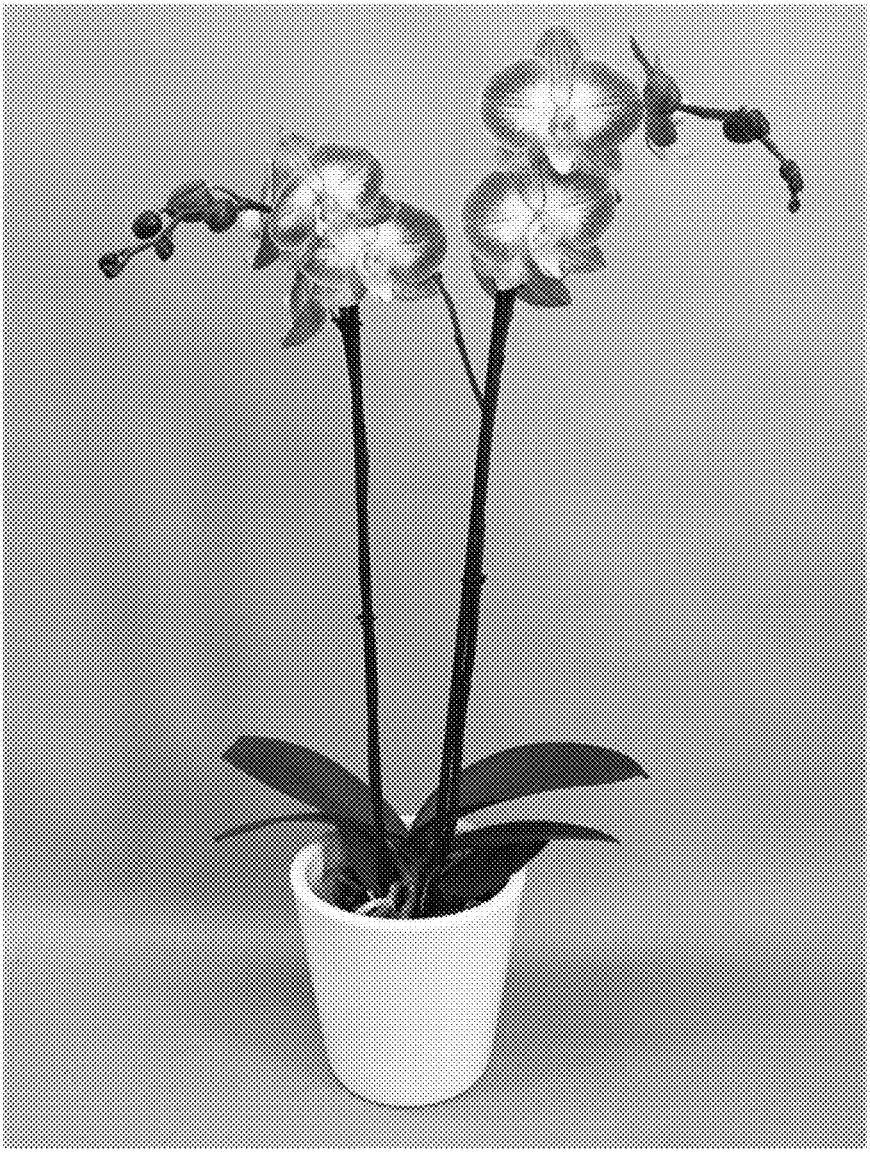
FIG. 1 shows the overall plant habit, including blooms, buds, and foliage of 'PHALIPUE'.
Figure 2:
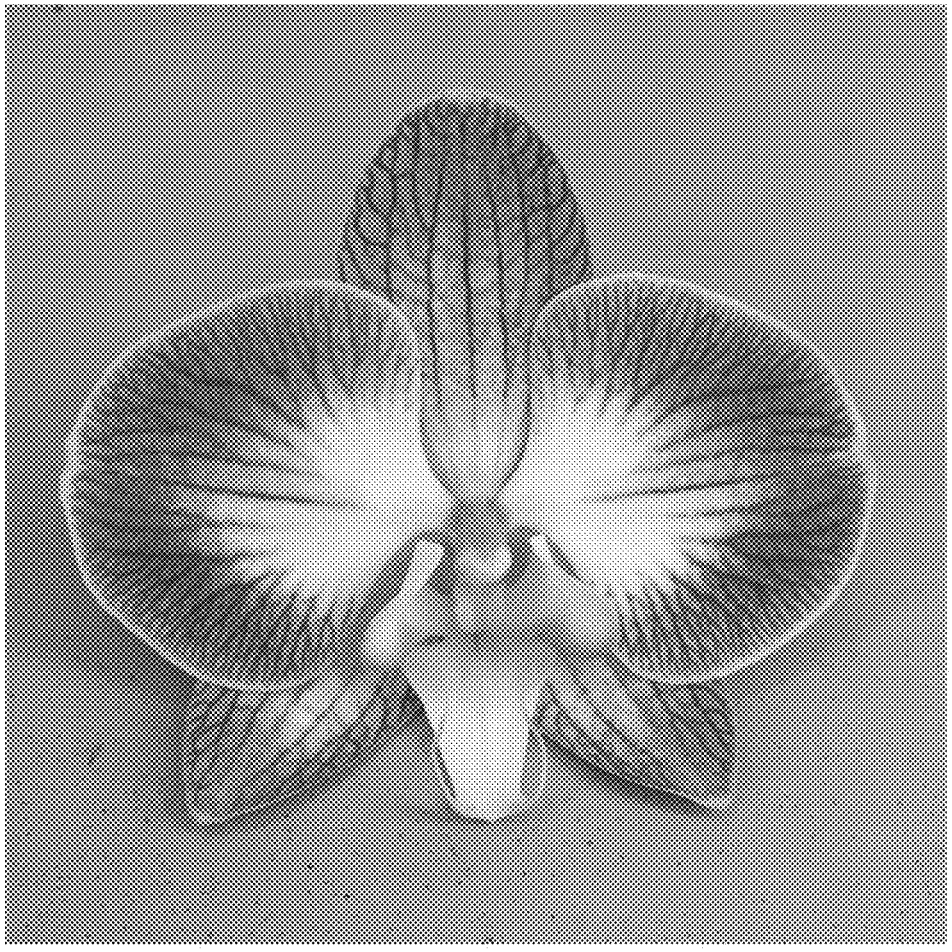
FIG. 2 shows a close-up of a flower of 'PHALIPUE'.
Figure 3:
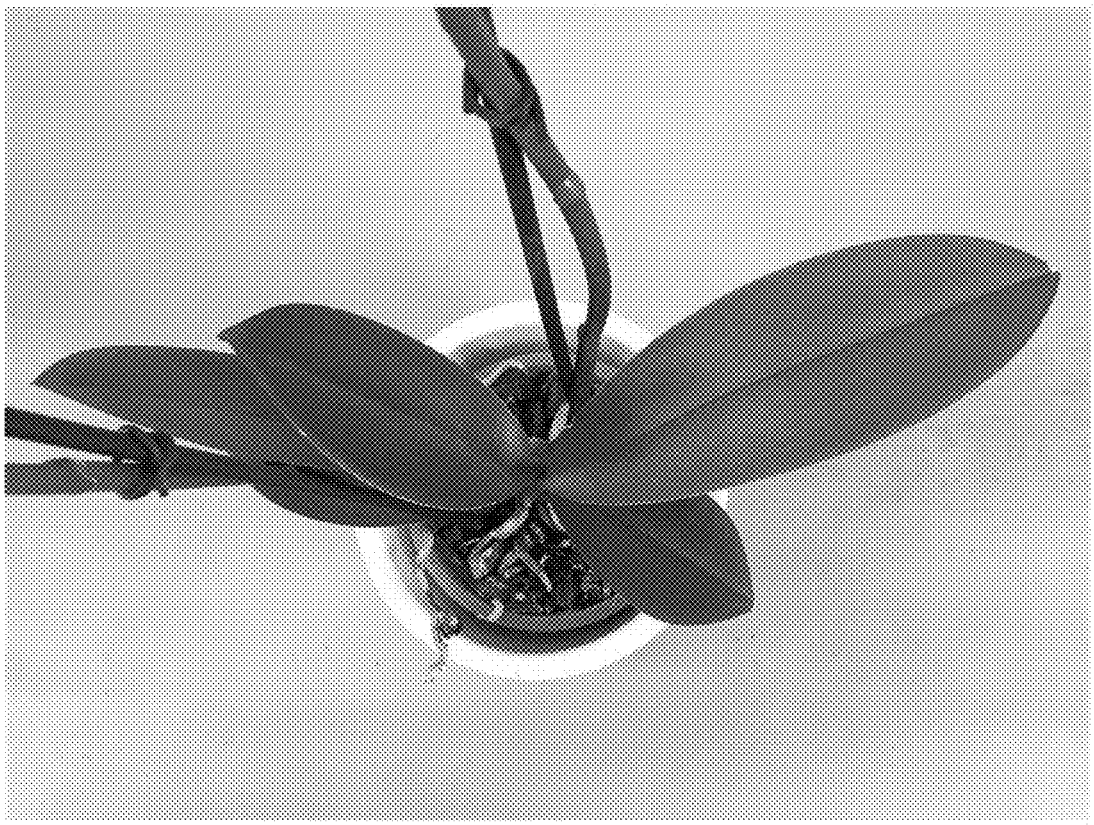
FIG. 3 shows an overhead view of the leaves of 'PHALIPUE'.

The following detailed description sets forth the distinctive characteristics of 'PHALIPUE'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in August 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALIPUE'.

Parentage:

*Female parent*.—*Phalaenopsis* cultivar '01-2994' (unpatented).

*Male parent*.—*Phalaenopsis* cultivar '32526-01' (unpatented).

Propagation:

*Type*.—Meristem tissue culture.

Roots:

*Root description*.—Greyed-green (a color in between RHS 190B and 190C) colored roots with branching lateral roots having light purple (a color in between RHS 76A and 76B) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 57.0 cm to 62.0 cm.

*Width* (*measured from leaf tips*).—About 29.0 cm to 32.0 cm.

*Vigor*.—Strong.

Leaves:

*Mature leaves*.—Quantity per plant: 6 to 8 leaves are produced before flowering. Length (fully expanded): 14.0 cm to 17.0 cm. Width: 6.0 cm to 7.0 cm. Position of the broadest part of the leaf: At the middle. Shape: Oblong. Base shape: Moderately elongated. Apex: Obtuse unequal. Leaf blade angle with the petiole (measured from the horizontal position): Between 10 degrees and 30 degrees. Leaf margin: Entire. Color: Upper surface: RHS 146A with a reddish-brown margin (RHS 200A). Lower surface: RHS 146B with very small reddish-brown dots and region (RHS 200A) toward the margin. Texture (both upper and lower surfaces): Smooth. Thickness: 2.2 mm to 2.5 mm. Variegation: Absent. Venation: Pattern: Parallel. Color of the midvein: Upper surface: RHS 146A. Lower surface: RHS 146B with a touch of reddish-brown (RHS 200B).

Peduncle:

*Quantity per plant*.—1 to 2.

*Number of flowers per peduncle*.—11 to 16.

*Length*.—57.0 cm to 62.0 cm.

*Diameter*.—5.0 mm to 6.0 mm.

*Strength*.—Strong.

*Aspect*.—Upright to slightly pendent.

*Texture*.—Smooth.

*Color*.—Mix of reddish-brown (RHS 200A) and green (RHS 146C).

*Internode length*.—3.0 cm to 4.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 230.0 mm to 300.0 mm.

*Flowering time*.—First flowers can be expected 10 to 11 months after planting in a 12-cm pot.

*Flower*.—Height: 70.0 mm to 75.0 mm. Diameter: 83.0 mm to 88.0 mm. Depth of lip: 27.0 mm to 29.0 mm.

*Flower longevity*.—On the plant: 14 to 16 weeks.

*Flower shape*.—Flat.

*Fragrance*.—Absent.

*Flower bud*.—Average size: Medium to large. Length: 21.0 mm to 23.0 mm. Width: 16.0 mm to 18.0 mm. Shape: Egg shaped. Color: Touch of yellow-green (RHS N144D) at the base; dark red-purple (a color in between RHS 187B and 187C) with a hint of yellow-green (RHS N144D).

*Petals*.—Arrangement: Open/free. Shape: Semi-circular. Apex: Emarginated asymmetric. Margin: Weakly undulated. Length (from base to tip): 39.0 mm to 41.0 mm. Width: 45.0 mm to 47.0 mm. Position of the broadest part of the petal: Toward the base. Color (when fully opened): Upper surface: Basic color: Reddish-purple (RHS N78B). Over color: White (RHS NN155C) at the base. Lower surface: Basic color: Light purple (RHS 76A) from the base toward centrum. Over color: White (RHS NN155C) at the base on sides; purplish-pink stripes (RHS N78C) toward edge. Number of spots and stripes on the petals (upper surface): Medium to many stripes. Color of spots and stripes on the petals (upper surface): RHS N78A. Density of netting of the petals (upper surface): None. Color of the netting (upper surface): None.

*Dorsal sepal*.—Shape: Elliptic. Apex: Emarginated symmetric. Margin: Entire. Length (from base to tip): 39.0 mm to 41.0 mm. Width: 25.0 mm to 27.0 mm. Position of the broadest part of the dorsal sepals: At the middle. Color (when fully opened): Upper surface: Basic color: Light reddish-purple (RHS N78D). Over color: Very light purple (RHS 76B) at the base. Lower surface: Basic color: Purplish-pink (RHS N78C). Over color: Reddish-purple midvein (RHS N78A). Number of spots and stripes on the dorsal sepals (upper surface): Medium to many stripes. Color of spots and stripes on the dorsal sepals (upper surface): RHS N78A. Density of netting of the dorsal sepals (upper surface): Low. Color of the netting: RHS N78A.

*Lateral sepals*.—Shape: Ovate. Apex: Obtuse asymmetric. Margin: Entire. Length (from base to tip): 41.0 mm to 43.0 mm. Width: 23.0 mm to 25.0 mm. Position of the broadest part of the lateral sepals: Toward the base. Color (when fully opened): Upper surface: Basic color: Purplish-pink (RHS N78C). Over color: White (RHS NN155C) and light yellow-green (RHS 145C) at the base. Lower surface: Basic color: Light reddish-purple (RHS N78D). Over color: Light yellow-green (RHS 145D) at the base; reddish-purple region (RHS N78B) and reddish-purple midvein (RHS N78A) toward the tip. Number of spots and stripes on the lateral sepals (upper surface): Medium stripes. Color of spots and stripes on the lateral sepals (upper surface): RHS N78A. Density of netting of the lateral sepals (upper surface): Medium. Color of the netting (upper surface): RHS N78A.

*Labellum* (*lip*).—Whiskers: Present. Length of whiskers: 17.0 mm to 19.0 mm. Color of whiskers: Light purple (RHS 76A) at the base with greenish-yellow tips (RHS 2B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 19.0 mm to 21.0 mm. Width: 13.0 mm to 15.0 mm. Color: Upper surface: Light greenish-yellow (a color in between RHS 4C and 4D) at the base and yellow (RHS 9A) on one side; white (RHS NN155C) toward the other side. Lower surface: Light yellow-green margin (RHS 4D) on one side; yellow (RHS 9A) on one side; white (RHS NN155C) toward the other side. Number of spots and stripes on the lateral lobe: None. Color of spots and stripes on the lateral lobe: Not applicable. Density of netting of the lateral lobe: None. Color of the netting: None.

*Apical lobe*.—Shape: Triangular. Margin: Entire. Length: 20.0 mm to 22.0 mm. Width: 17.0 mm to 19.0 mm. Color: Upper surface: Yellow (RHS 7A) at the base; white (RHS NN155C) toward whiskers. Lower surface: Yellow wings (RHS 7A); white (RHS NN155C) toward whiskers; very light purple (RHS 76C) in the middle with a touch of light purple (RHS 76A) toward whiskers. Number of spots and stripes on the apical lobe: None. Color of spots and stripes on the apical lobe: Not applicable. Density of netting of the apical lobe: None. Color of the netting: None.

*Callus*.—Average size: Medium. Height: 6.0 mm to 7.0 mm. Length: 4.0 mm to 5.0 mm. Width: 4.0 mm to 5.0 mm. Color: Light yellow-green (RHS 4D) on sides; greenish-yellow (RHS 6A) toward the tip; yellow margin (RHS 9A) on front.

Reproductive organs:

*Column*.—Length: 9.0 mm to 11.0 mm. Diameter: 4.9 mm to 5.3 mm. Color: Purplish-pink (RHS N78C).

*Pollinia*.—Quantity: 2. Diameter: 0.8 mm to 1.0 mm. Color: Orange (RHS 24A).

*Ovary*.—Length: 9.0 mm to 11.0 mm. Diameter: 2.2 mm to 2.4 mm.

*Pedicel*.—Length: 34.0 mm to 36 .0 mm. Diameter: 2.6 mm to 3.0 mm. Texture: Smooth. Color: Hint of light yellow-green (RHS 146D) at the base and very light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALIPUE' differs from female parent plant '01-2994' (unpatented) in that 'PHALIPUE' has apical lobes with a main color of white, purplish-pink columns, and no petal twisting, whereas '01-2994' has apical lobes with a main color of white with a touch of light purple, white columns, and petal twisting present.

'PHALIPUE' differs from male parent plant '32526-01' (unpatented) in that 'PHALIPUE' has apical lobes with a main color of white and purplish-pink columns, whereas '32526-01' has apical lobes with a main color of dark red and reddish-purple columns. Additionally, 'PHALIPUE' has smaller flowers than '32526-01'.

'PHALIPUE' is most similar to the commercial *Phalaenopsis* plants named 'PHALVAPYH' (U.S. Plant Pat. No. 31,052) and 'PHALMACHE' (unpatented). 'PHALIPUE' differs from the commercial variety 'PHALVAPYH' in that 'PHALIPUE' has whiskers that are light purple at the base with greenish-yellow tips, whereas 'PHALVAPYH' has whiskers that are reddish-purple. Additionally, 'PHALIPUE' has smaller flowers and longer whiskers than 'PHALVAPYH'.

'PHALIPUE' differs from the commercial variety 'PHALMACHE' in that 'PHALIPUE' has apical lobes with a main color of white and whiskers that are light purple at the base with greenish-yellow tips, whereas 'PHALMACHE' has apical lobes with a main color of reddish-purple and whiskers that are red. Additionally, 'PHALIPUE' has smaller flowers and longer whiskers than 'PHALMACHE'.

I claim:

1. A new and distinct variety of *Phalaenopsis* plant named 'PHALIPUE', substantially as described and illustrated herein.

* * * * *